United States Patent [19]

Massardo et al.

[11] 4,388,323

[45] Jun. 14, 1983

[54] ACARICIDE COMPOUNDS

[75] Inventors: Pietro Massardo; Angelo Longoni; Paolo Piccardi, all of Milan, Italy

[73] Assignee: Montedison S.p.A., Milan, Italy

[21] Appl. No.: 244,591

[22] Filed: Mar. 17, 1981

[30] Foreign Application Priority Data

Mar. 28, 1980 [IT] Italy ............................ 21003 A/80
Nov. 25, 1980 [IT] Italy ............................ 26205 A/80
Dec. 3, 1980 [IT] Italy ............................ 26401 A/80

[51] Int. Cl.$^3$ .................. C07C 69/74; C07C 43/235; A01N 53/00; A01N 31/14
[52] U.S. Cl. .................................... 424/305; 424/308; 424/311; 424/341; 560/1; 560/106; 560/122; 560/123; 560/124; 560/254; 568/649; 568/654
[58] Field of Search .................. 568/654; 560/124, 1, 560/106, 254, 122, 123; 424/305, 308, 311, 341

[56] References Cited

U.S. PATENT DOCUMENTS

| | | | |
|---|---|---|---|
| 3,190,908 | 6/1965 | Pyne | 560/254 |
| 3,732,254 | 5/1973 | Sidall | 568/654 |
| 3,933,804 | 1/1976 | Schelling | 568/654 |
| 3,950,328 | 4/1976 | Karrer | 568/654 |
| 3,995,054 | 11/1976 | Henrick et al. | 424/305 |
| 4,000,315 | 12/1979 | Henrick | 424/305 |
| 4,061,683 | 12/1977 | Karrer | 260/613 R |
| 4,126,623 | 11/1978 | Piccardi et al. | 260/340.5 R |
| 4,140,794 | 2/1979 | Piccardi et al. | 424/282 |
| 4,162,328 | 7/1979 | Zurflah | 560/124 |
| 4,169,151 | 9/1979 | Massardo et al. | 424/282 |

*Primary Examiner*—Michael L. Shippen

[57] ABSTRACT

There are described hydroquinone-diethers endowed with a high acaricide activity, the processes for their preparation and their use as acaricides.

22 Claims, No Drawings

ACARICIDE COMPOUNDS

THE PRESENT INVENTION

The present invention concerns acaricide compounds and more particularly it relates to new hydroquinone-diethers, their preparation processes, their use as acaricides and acaricide compositions containing them.

Many products are known to be endowed with an acaricide activity, some being active on mite eggs, others being effective against neanidae or mite adults.

The known acaricides belong to various different chemical classes such as that of: organo-phosphorous compounds, halo-aromatic compounds, carbamates, metal-organic compounds, etc.

The main known acaricide compounds have been listed by J. C. Street in "Basis for Selectivity of Acaricides", chap. VIII, page 155; in "Pesticide Selectivity", Dekker Inc.-New York (1975).

Recently have been described cyclopropanecarboxylates endowed with acaricide active (U.S. Pat. No. 3,995,054 Zoecon). In the literature have been reported also some aromatic ethers endowed with juvenile hormones activity and possessing at the same time a certain degree of acaricidal activity. Examples of such compounds are those described in U.S. Pat. No. 4,061,683 (Ciba Geigy) and in U.S. Pat. Nos. 4,140,794, 4,126,623, 4,169,151 and Belgian Pat. No. 877,164 (Montedison S.p.A.).

In spite of the great variety of known acaricide compounds, mites remain still a serious problem because of the damages they cause to the crops, in fact during one season they reproduce in several generations, thus facilitating the appearance of resistance phenomena to the acaricide products used.

We have now found and this forms an object of this invention, compounds of general formula:

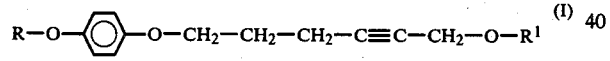

wherein:
R represents an alkyl with from 8 to 11 carbon atoms
$R^1$ represents an hydrogen atom, an alkyl with from 1 to 4 carbon atoms, alkenyl with from 2 to 4 carbon atoms or

wherein
$R^2$ represents an alkyl with from 1 to 4 carbon atoms, a cycloalkyl with from 3 to 6 carbon atoms or phenyl.

The compounds of formula I are endowed with a high acaricide activity being particularly effective against mite eggs and displaying at the same time a certain activity against adult mites.

The above mentioned compounds are endowed also with a high activity against overwintering eggs of mites and this is a quite peculiar characteristic because most of the known acaricide compounds prove to be inactive on this type of eggs. The compounds of formula I, moreover, are endowed with a practically negligible toxicity towards warm-blooded animals and fish being at the same time characterized by the absence of phytotoxicity, even at high dosages on the most diffused crops and thus can be conveniently utilized for controlling mite infestations.

Thus, objects of this invention are a method for controlling mite infestations on useful crops consisting in applying on the plants an effective amount of a compounds of formula I as such or in the form of suitable compositions and the acaricide compositions having as active ingredient a compound of formula I.

Still other objects of this invention consist in a method for controlling mite infestations on useful plants by treating the overwintering eggs with a compound of formula I as such or in the form of suitable composition and the acaricide compositions active against the mites overwintering eggs containing as active ingredient a compound of formula I.

The preparation of the compounds of formula I can be obtained according to reactions generally known in the normal procedures of organic chemistry.

In the general description of the synthetic procedures herebelow reported the symbols R, $R^1$ and $R^2$ have the same meanings as those reported for formula I when not otherwise specified.

A suitable starting product is a hydroquinone monoalkyl ether of formula:

Compounds of formula (A) are known or can be easily prepared according to known methods, for instance as described in "Journal of Pharmaceutical Society of Japan" 74, 875 (1954) [Chemical Abstract 49, 9543 d].

Compounds of formula (A) are then converted into their diether-derivatives. Intermediate in these reactions are the alkaline salts of formula:

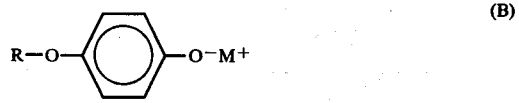

(wherein M+ represents an alkaline cation) which are easily obtained by treating compounds (A) with alkaline bases. From salts (B) the synthesis process develops according to different alternative procedures.

(1) The compounds of formula I in which $R^1$ is an alkyl or alkenyl group can be obtained by reacting a salt of formula (B) with a compound of formula:

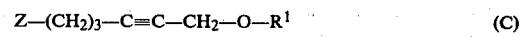

[wherein $R^1$ is an alkyl or alkenyl group and Z is a leaving group such as a chlorine or bromine atom or a tosylate (p.toluenesulphonate) of formula p.CH$_3$—C$_6$H$_4$—SO$_2$—O—]. Compounds of formula (C) can be obtained by reacting a propargyl ether of formula:

(wherein $R^1$ is an alkyl or alkenyl group) with a strong base such as butyl-lithium and by reacting the lithium salt thus obtained with derivatives of 3-chloro (or 3-bromo)-1-propanol in which the hydroxy group has been previously protected for instance in the form of acetal. Thereby are obtained alcohols of formula (C) (wherein Z=OH). From these the compounds of formula (C) wherein Z has the hereabove reported meanings are easily obtained by substitution or by reaction with tosyl-chloride.

(2) Another procedure for the preparation of the compounds of formula I in which $R^1$ is an alkyl or alkenyl group consists in reacting the alkaline salt (B) with 1,3-dibromo-propane thereby obtaining a compound of formula:

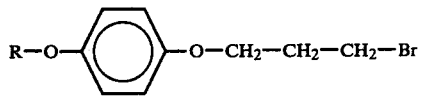
(E)

Compound (E) is then condensed in the presence of a strong base with a propargyl-ether of formula:

 (D)

(wherein $R^1$ is an alkyl or alkenyl group).

(3) A general procedure for the preparation of the compounds of formula I consists in reacting the salt (B) with 1,1,1,5-tetrachloropentane ($Cl_3C-CH_2-CH_2-CH_2-CH_2Cl$) in an inert solvent and in the presence of an excess of a strong base, thereby obtaining a compound of formula:

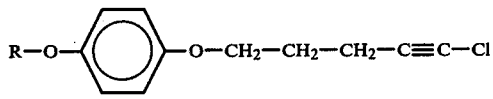
(F)

which is then treated with butyl-lithium in an anhydrous inert solvent at low temperature, thereby obtaining the lithium salt of formula:

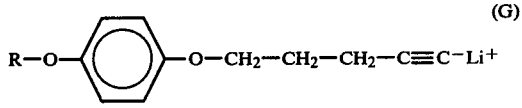
(G)

The reaction of salt (G) with an ether of formula:

$Cl-CH_2-O-R^1$ (H)

(wherein $R^1$ is an alkyl or alkenyl group) affords the compounds of formula I in which $R^1$ represents an alkyl or alkenyl group. By reacting the salt (G) with formaldehyde, the compounds of formula I in which $R^1$ is a hydrogen atom are obtained. From these, by reaction with an acyl-chloride of formula:

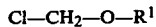 (J)

the compounds of formula I in which $R^1$ is a

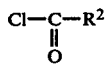

group are obtained.

(4) The lithium-salts of formula (G) can also be obtained by reacting the salt (B) with a 5-halo-1-pentyne of formula:

$Z'-CH_2-CH_2-CH_2-C\equiv CH$ (K)

(wherein $Z'$=Cl, Br) thereby obtaining a compound of formula:

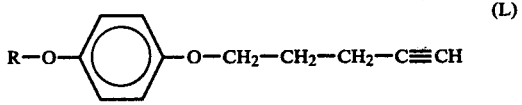
(L)

which is then converted into salt (G) by treatment with butyl-lithium.

Moreover, it must be pointed out that the peculiar structure of the compounds of formula I is suited for following other synthetic procedures.

For instance, starting from a hydroquinone mono-alkaline salts of formula:

(M)

(wherein $M^+$ is an alkaline cation) and by using methods similar to those described under points 1 to 4, it is possible to prepare compounds of formula:

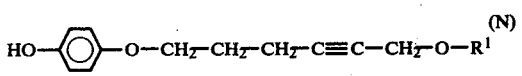
(N)

From these, by treatment with alkaline bases and by reaction with compounds of formula:

R—Z (P)

(wherein Z=Cl, Br, tosyl ester) the compounds of formula I are obtained.

The compounds reported in the following Table 1 have been prepared by the methods hereabove described.

TABLE 1

Compounds of formula[a]:

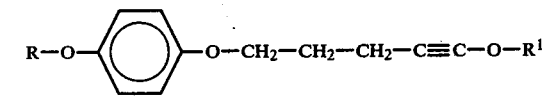

| Compound[b] n° | R | $R^1$ |
|---|---|---|
| 1[c] | $CH_3-(CH_2)_9-$ | $CH_3$ |
| 2 | $CH_3-(CH_2)_{10}-$ | $CH_3$ |
| 3 | $CH_3-(CH_2)_7-$ | $-CH(CH_3)_2$ |
| 4 | $CH_3-(CH_2)_7-$ | $CH_3$ |
| 5 | $CH_3-(CH_2)_7-$ | $C_2H_5$ |
| 6[d] | $CH_3-(CH_2)_9-$ | H |
| 7 | $CH_3-(CH_2)_9-$ |  |
| 8 | $CH_3-(CH_2)_9-$ | $-\underset{\underset{O}{\|}}{C}-CH_3$ |

TABLE 1-continued

Compounds of formula[a]:

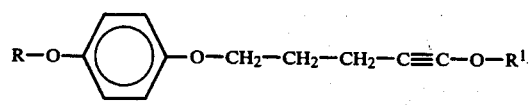

| Compound[b] n° | R | R¹ |
|---|---|---|
| 9 | $CH_3-(CH_2)_9-$ | $-\underset{\underset{O}{\|\|}}{C}-CH(CH_3)_2$ |
| 10 | $CH_3-(CH_2)_9-$ | $-CH_2-CH=CH_2$ |

Notes to Table 1
[a] The Infra-red (IR) and Nuclear Magnetic Resonance ($^1H$—NMR) spectroscopic data are consistent with the assigned structures.
[b] With the exception of compounds 1 and 6, all the listed compounds are thick oils at room temperature.
[c] Melting point = 33-34° C.
[d] Melting point = 66° C.

On the following Table 2 have been reported the ranges of the $^1H$—NMR signals of the radicals forming the compounds of Table 1.

Tenuipalpidae. The acaricide activity level of the compounds of formula I is, in most cases, by far higher than that of known acaricide compounds.

According to our experimental data, just for exemplifying purposes, compound No. 1 of Table 1 has an $LC_{50}$ (concentration that prevents the hatching of 50% of the eggs and corresponds to a 50% mortality) on *Tetranychus urticae* eggs that is about 100 times lower than that of compound 1-[(pent-4-yn-1-yl)-oxy]4-phenoxy-benzene, according to U.S. Pat. No. 4,061,683.

In Table 3 have been reported the acaricide activity data at the indicated doses of compounds according to this invention, expressed by the following scale.

5 = 100% of unhatched eggs
4 = 80-99% of unhatched eggs
3 = 60-79% of unhatched eggs
2 = 40-59% of unhatched eggs
1 = 20-39% of unhatched eggs
0 = 0-19% of unhatched eggs The acaricide activity has been considered particularly against two mite species (*Tetranychus urticae* and *Panonychus ulmi*) which are considered as particularly representative and significant owing to the extent of the crop damages and to their wide diffusion.

TABLE 2

$^1H$—NMR signals (δ, ppm), solvent = $CDCl_3$, internal standard: TMS

| R | $-O-\text{C}_6\text{H}_4-O-$ | $-CH_2-CH_2-CH_2-C\equiv$ | $\equiv C-CH_2-O$ | R¹ |
|---|---|---|---|---|
| 0.88-0.92 ($CH_3$) | 6.7-6.85 | 3.9-4.6 ($-O-CH_2-$) | 4.05-4.6 | 3.3-3.4 ($OCH_3$) |
| 3.5-4.1 ($CH_2-O-$) | (aromatic | 2.3-2.4 ($-CH_2-C\equiv$) | | 1.25 ($O-CH_2-CH_3$) |
| 1.1-2.6 (other | protons) | 1.8-1.9 ($-CH_2-$ | | 3.5 ($O-CH_2-CH_3$) |
| methylen | | $-CH_2-CH_2-$) | | 1.15 [$O-CH(CH_3)_2$] |
| groups | | | | 3.7 [$O-CH(CH_3)_2$] |
| | | | | 5-6.2 (allylic pattern, compound N° 10) |
| | | | | 2.3 (OH, compound N° 6) |
| | | | | 2.0 ($O-CO-CH_3$) |
| | | | | 0.7-1.05 [$(CH_2)_2$ in $O-CO-\triangleleft$] |
| | | | | 1.55 [CH in $O-CO-\triangleleft$] |
| | | | | 1.1 [$O-CO-CH(CH_3)_2$] |
| | | | | 2.4 [$O-CO-CH(CH_3)_2$] |

As previously indicated, the compounds of general formula I are endowed with a high acaricide activity. Said compounds are particularly active against mite eggs and they possess at the same time a certain activity against adult mites. The compounds of formula I are, moreover, characterized by a high residual activity, a very important characteristic for ovicidal compounds, by a very low toxicity for warm-blooded animals and fish and by the absence of phytotoxicity.

The most important mite pests from an economical point of view because of the crop damages they cause and of their wide diffusion in all cultivated areas, belong mainly to the Tetranychidae Family, genera: Tetranychus (*T. urticae, T. telarius, T. pacificus*, etc.) Panonychus (*P. ulmi, P. citri*, etc.), Bryobia (*B. preatiosa*) and Oligonychus.

Other species harmful to cultivations are present for instance, in the following Families Eriophydae (genera: Aceria, Eriophyes, Phyllocoptes, Phyllocoptruta, Vasates, etc.) Tarsone midae (genus Hemitarsonemus) and The activity data reported on Table 3 have been determined as described in example 6.

TABLE 3

Acaricide activity of compounds of the invention at the indicated doses expressed by a scale of values from 5 (complete activity) to 0 (negligible if any activity).

| Compound No. (see Table 1) | Dose (% a.i.) | T. urticae (eggs) | P. ulmi (summer eggs) |
|---|---|---|---|
| 1 | 0.1 | 5 | 5 |
|   | 0.01 | 5 | 5 |
|   | 0.001 | 5 | 5 |
| 2 | 0.1 | 5 | 5 |
|   | 0.01 | 5 | 5 |
|   | 0.001 | 4 | 4 |
| 4 | 0.1 | 5 | 5 |
|   | 0.01 | 5 | 5 |
|   | 0.001 | 4 | — |
| 6 | 0.1 | 5 | 5 |
|   | 0.01 | 5 | 5 |
|   | 0.001 | 5 | 4 |

TABLE 3-continued

Acaricide activity of compounds of the invention at the indicated doses expressed by a scale of values from 5 (complete activity) to 0 (negligible if any activity).

| Compound No. (see Table 1) | Dose (% a.i.) | T. urticae (eggs) | P. ulmi (summer eggs) |
| --- | --- | --- | --- |
| 7 | 0.1 | 5 | 5 |
| | 0.01 | 5 | 5 |
| | 0.001 | 4 | 4 |
| 8 | 0.1 | 5 | 5 |
| | 0.01 | 5 | 4 |
| | 0.001 | 4 | — |
| 9 | 0.1 | 5 | 5 |
| | 0.01 | 5 | 5 |
| | 0.001 | 4 | 4 |
| 10 | 0.1 | 5 | 5 |
| | 0.01 | 5 | 5 |
| | 0.001 | 5 | 4 |
| A[a] | 0.1 | 5 | — |
| | 0.01 | 3 | — |
| | 0.001 | 0 | — |
| B[b] | 0.1 | 5 | 5 |
| | 0.01 | 4 | 4 |
| | 0.001 | 1 | 0 |

Notes to Table 3
[a]Compound A = 1-[(pent-4-yn-1-yl)-oxy]-4-phenoxy-benzene (U.S. Pat. No. 4,061,683)
[b]Compound B = hexadecyl-cyclopropanecarboxylate (U.S. Pat. No. 3,995,054).

The compounds of the present invention are endowed with a high persistence of acaricide activity and this, as herein before mentioned, is an important characteristic for ovicide compounds. In fact, mite pests reproduce with several generations during the growing season and the high persistence of activity of the compounds of Table 1 allows to reduce the number of acaricide treatments.

The persistence data of some representative compounds of Table 1 in comparison to those of two known compounds, are reported on the following Table 4.

The persistence has been determined by the procedure described in example 7. The data of Table 4 are expressed by the same scale of values used for the data of Table 3.

TABLE 4

Persistence of acaricide activity against summer eggs of Panonychus ulmi expressed by a scale of values from 5 (complete activity) to 0 (negligible if any activity).

| Compound No. | Dose (% a.i.) | Activity after 3 days[a] | Activity after 13 days[a] |
| --- | --- | --- | --- |
| 1 | 0.05 | 5 | 5 |
| 4 | 0.05 | 5 | 4 |
| 6 | 0.05 | 5 | 5 |
| 9 | 0.05 | 5 | 5 |
| 10 | 0.05 | 5 | 5 |
| A[b] | 0.05 | 3 | 0 |
| B[b] | 0.05 | 4 | 0 |

Notes to Table 4
[a]Days elapsed from the treatment to the infestation.
[b]Reference compounds, see Notes to Table 3.

The acaricide compounds of general formula I may be usefully applied in the control of mites as such or in the form of suitable compositions or formulations.

In the compositions or formulations, besides one or more compounds of general formula I as active ingredient, there may be present suitable solid and liquid vehicles and additives such as surfactants, wetting agents, adhesive agents and dispersants.

The compounds may be formulated as emulsifiable concentrates, emulsious, solutions, wettable powders, pastes, powders etc., according to normal techniques in the formulative pratice. If required by particular purposes such as for instance the necessity to expand the activity range or because of the environmental conditions, other active substance (adulticides or insecticides) can further be added to the above described compositions or formulations.

The co-formulable active substances, amongst others, comprise: organo-phosphorous compounds, pyrethroids, nitrophenols, formamidines, ureic derivatives, carbamates, chlorinated hydrocarbons and metal-organic compounds.

In the above cited compositions the active ingredient may be present in quantities comprised between 0.5 and 90% by weight, depending on the type of composition and on the kind of treatment needed.

The amount of composition to be distributed in the area to be protected against mite infestations, depends on various factors such as for instance: the type of composition or formulation, the type of application, the infesting species and the level of infestation, the type of cultivation to be protected, the climatic and environmental conditions.

At any rate, the active ingredient must be distributed in quantities comprised between 0.1 and 3 Kg/ha.

As herein before mentioned, the compounds of formula I are active also against overwintering eggs of mites.

As far as the ovicide activity on mites is concerned, a distinction has to be made between the activity against summer eggs and that against overwintering eggs. In fact, some mite species overwinter in the stage of eggs and these winter eggs are less sensitive to pesticides in comparison to summer eggs. This is due to the state of quiescence of the embryonal life as well as to the barrier that the chorion of the winter eggs, more resistant than that of the summer eggs, offers to the penetration of the acaricide compound.

Because of the particular characteristics of the winter eggs of mites, the greatest part of the known acaricide compounds prove to be inactive on this kind of eggs.

Other compounds prove to be only partially active and exclusively during the very short period of time close to the hatching of the eggs.

Presently the winter control of mite eggs is generally conducted by applying formulations of phosphoric esters (for instance Parathion) in mineral oils. Also in this case, the effectiveness of such formulations is never complete and is achieved only by treating in coincidence with the hatching of the eggs.

In the short period of time in which such a treatment may be useful, there are often adverse weather conditions. A treatment before the above mentioned period proves little effective on winter eggs because they are particularly resistant to the penetration of the pesticides. On the other hand, a delayed treatment may produce phenomena of phytotoxicity inasmuch as the advanced vegetative stage of plants is sensitive to many mineral oils.

The availability of specific products active against winter eggs would allow to carry out treatments in deep winter, thereby eliminating the aforementioned difficulties and at the same time offering the advantage of not causing a damage to numerous species of insects useful for controlling mites (predatory insects). Moreover, from a practical point of view, the possibility to protect the cultivations from mite attacks in winter time, that is, during a period in which the work on the farm is limited, represents a further undoubted advantage.

As far as we know, there are no specific acaricide compounds on the market that are active against winter eggs of mites.

The effectiveness of formula I compounds against the winter eggs is more than satisfactory for a practical use in agriculture. In fact the compounds of formula I are endowed with a high acaricide activity against the winter eggs even at rather low doses.

Moreover, said compounds, when applied in the right manner so as to reach all the mite eggs, exert a practically total acaricide activity and, consequently, the plants remain disinfested for a long period of time (even for two months after the period of hatching of the eggs), thus allowing to considerably delay the treatments against the mites which may be present later on as a consequence of re-infestations of a different origin.

The known products used against the winter eggs of mites (for instance mineral oils additioned with phosphoric esters), besides the afore mentioned applicational drawbacks, do not possess a complete activity and thus, in order to obtain the same results, it is necessary to carry out at least further two spring treatments with acaricide products.

For practical applications in agriculture, it is better to use the compounds of formula I in the form of suitable compositions, with the main scope of obtaining the best possible distribution of the product so as to reach all the mite eggs which are often placed on parts of the plants that are difficult to be reached.

The above indicated compositions may contain, besides one or more of the compounds of formula I as active ingredient, an inert vehiculating agent and other additives.

The choice of the vehicle and of the additives depends on the type of formulation needed.

Suitable formulations are the emulsifiable concentrates that consist of the active ingredient, of a liquid vehiculant such as an organic solvent, and of surfactants. Examples of organic solvents that may be used in the above mentioned compositions, are the aromatic or alkylaromatic hydrocarbons such as for instance xylol or other commercial mixtures of alkylaromatic hydrocarbons, alcohols such as butyl or isoamyl alcohol, ketones such as ethyl-amyl-ketone or cyclohexanone.

Examples of surfactants that may be used in the above cited compositions, are alkylbenzensulphonates, polyoxyethylated alkylphenols, polyoxyethylated vegetable oils, glycerides of polyoxyethylated fatty acids, polyoxyethylated sorbitan oleates or mixtures thereof.

In the above cited compositions the ingredients may be present in the following quantities:

| | |
|---|---|
| A - Active ingredient (compound of formula I) | 0.5–50% by weight |
| B - Organic solvent | 30–80% by weight |
| C - Surfactant | 0.5–20% by weight |

It is well known that the mineral oils possess a certain activity against the winter eggs of mites. Such activity, which, however, is not very pronounced, is due essentially to an activity of a physical character, inasmuch as said oils may cover with a very thin film the mite eggs thus hindering the gaseous exchanges and thus often even causing the death of the embryo.

It is, thus, possible to add to the above described compositions also mineral oils with the function of vehicles but at the same time also of an active substance.

The suitable mineral oils are the commercial oils having a content in unsulphonable substances greater than or equal to 80%. The solvents and surfactants that may be used are those mentioned previously.

In these compositions the ingredients may be present in the following amounts:

| | |
|---|---|
| A - Compound of formula I | 0.5–30% by weight |
| B - Mineral oil | 40–80% by weight |
| C - Organic solvent | 5–30% by weight |
| D - Surfactant | 0.5–20% by weight |

Whenever a special situation should require it, it is possible to add to the compositions or formulations hereabove described other active substances useful for the winter control of other plant pests and diseases.

Said active substances may comprise insecticides, but above all, fungicides.

The mite species that may be effectively controlled in the stage of winter eggs with the method and the compositions objects of this invention, belong to the family Tetranychidae, genera Panonychus, Bryobia, and Oligonychus.

Amongst these species, the most important one for the extent of the damages inflicted to the plants and for the wide diffusion in all temperate areas, is *Panonychus ulmi* which almost everywhere shows a high level of resistance to the different pesticides due to the intensive chemical attack to which it is systematically subjected.

In the following Table 5 have been reported the activity data against winter eggs of *Panonychus ulmi* of some compounds of the invention and of some known compounds. The activity data reported on Table 5 have been determined according to the procedure described in example 8 and expressed by the following scale:

++++ = practically complete acaricide activity
+++ = high activity
++ = partial activity
+ = negligible if any activity.

From the data reported on Table 5, it appears that the compounds of the invention possess a high activity against mites winter eggs. Said activity is high even when they are tested as simple hydroacetonic solutions and becomes practically complete when they are formulated, independently from the presence of a mineral oil.

TABLE 5

| Acaricide activity against *P. ulmi* winter eggs | | | |
|---|---|---|---|
| Active ingredient | Formulation[a] | Dose a.i. (%) [% min. oil] | Acaricide activity |
| Compound No. 1 | Hydroacetonic solution | 0.05 | ++++ |
| | | 0.01 | +++ |
| | EC 20 | 0.05 | ++++ |
| | | 0.01 | ++++ |
| | EC 20 + mineral oil | 0.01 [2] | ++++ |
| Compound No. 2 | Hydroacetonic solution | 0.05 | +++ |
| | | 0.01 | ++ |
| Compound No. 6 | EC 20 | 0.05 | ++++ |
| | | 0.01 | ++++ |
| | EC 20 + mineral oil | 0.01 [2] | ++++ |
| Compound No. 9 | EC 20 | 0.05 | ++++ |
| | | 0.01 | ++++ |
| | EC 20 + mineral oil | 0.01 [2] | ++++ |
| Compound No. 10 | EC 20 | 0.05 | ++++ |
| | | 0.01 | ++++ |
| | EC 20 + mineral oil | 0.01 [2] | ++++ |
| Compound A[b] | EC 20 | 0.05 | + |
| | | 0.01 | + |
| | EC 20 + mineral oil | 0.01 [2] | ++ |
| Parathion[c] | Commercial formulate | 0.06 [0.96] | ++ |

TABLE 5-continued

Acaricide activity against P. ulmi winter eggs

| Active ingredient | Formulation[a] | Dose a.i. (%) [% min. oil] | Acaricide activity |
|---|---|---|---|
| in mineral oil | | | |
| Mineral oil[a] | — | [2] | ++ |

Notes to Table 5
[a]EC 20 = Emulsifiable concentrate at 20% by weight of active ingredient.
Mineral oil = Emulsion of mineral oil (80% by weight) having an unsulphonable content greater than 80%, and water.
EC 20 + mineral oil = mixture prepared at the moment of the treatment.
[b]Compound A = Reference compound, see note to Table 3.
[c]Parathion = common name for the compound O,O—diethyl-O—p.nitro phenyl-phosphorothioate.

On the following Table 6, have been reported examples of compositions according to this invention.

The compositions can be prepared by simply mixing together the ingredients, at room temperature.

The compositions containing also mineral oils are prepared by admixing the oil to the mixture of the other ingredients.

In the following Table 6, the quantities of the ingredients are expressed as percentages by weight.

TABLE 6

Acaricide compositions for controlling mites winter eggs (percentages by weight)

| Components | | 1 | 2 | 3 | 4 | 5 | 6 | 7 | 8 | 9 |
|---|---|---|---|---|---|---|---|---|---|---|
| Compound of formula I (%) | | 20 | 20 | 20 | 10 | 50 | 5 | 5 | 20 | 2.5 |
| Mineral Oil (%) | JS-1[a] | | | | | | 80 | | 45 | 80 |
| | Process-oil 507[b] | | | | | | | 80 | | |
| Solvent (%) | Xylol | 70 | | | 80 | 40 | 7 | 7 | 25 | 9.5 |
| | Isobutyl alcohol | | 70 | | | | | | | |
| | Cyclohexanone | | | 70 | | | | | | |
| Surfactant (%) | Emulsion 7B[c] | 4.9 | 4.9 | 4.9 | 4.9 | 4.9 | 5 | 5 | 7 | 5 |
| | Setrolene O[d] | 2.1 | 2.1 | 2.1 | 2.1 | 2.1 | 3 | 3 | 3 | 3 |
| | Agrol Ca/L[e] | 3 | 3 | 3 | 3 | 3 | | | | |

Note to Table 6
[a]"JS-1" = registered trade mark of "Industria Italiana Petroli" for a mineral oil having a content in unsulphonable substances greater than or equal to 90%.
[b]"Process-oil 507" = registered trade mark of "Societa I.P." for a mineral oil with a content in unsulphonable substances greater than or equal to 90%.
[c]"Emulsion 7B" = registered trade mark of "ROL Company", for polyoxyethylated alkyl-phenols.
[d]"Setrolene O" = registered trade mark of "ROL Company", for polyoxylated sorbitan-oleate.
[e]"Agrol Ca/L" = registered trade mark of "ROL Company", for calcium alkylbenzenesulphonate.

With the purpose of still better illustrating the invention, the following examples are given.

EXAMPLE 1

Preparation of 1-undecyloxy-4-[(7-oxa-4-octynyl)-oxy]-benzene (compound No. 2; Table 1).

(A) Preparation of 1-undecyloxy-4-[(5-chloro-4-pentynyl)oxy]-benzene

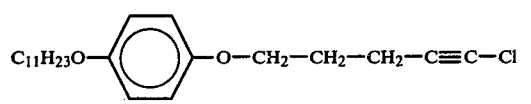

Into a 500 ml flask, fitted with a stirrer, a thermometer, a reflux condenser and a dripper funnel, there were introduced:

- 12 g of 4-undecyloxy-phenol 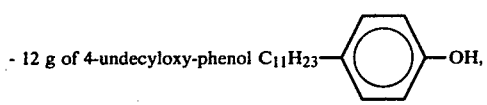

- 150 ml of DMSO,

- 5.733 g of ground NaOH (in a molar ratio soda/phenol greater than 3:1).

This mixture was vigorously stirred at room temperature and was additioned slowly dropwise, with:

10.5 g of 1,1,1,5-tetrachloropentane $ClCH_2$—$CH_2$—$CH_2$—$CH_2$—$CCl_3$.

At the end of the dripping, the temperature was raised to 60°–70° C. and maintained there for 4 hours, whereafter it was allowed to rest overnight at room temperature.

The mixture was then poured into water and extracted with ethyl ether.

The organic phase was washed with water up to a neutral pH, then dried on anhydrous magnesium sulphate and the solvent was then evaporated.

There were thus obtained 15.3 g of the crude product which was purified by chromatography on silica gel (eluent: petroleum ether-ethyl ether in a 95:5 ratio).

The IR analysis proved consistent with the assigned structure.

(B) Metalation of 1-undecyloxy-4-[(5-chloro-4-pentynyl)-oxy]benzene with lithium-butyl

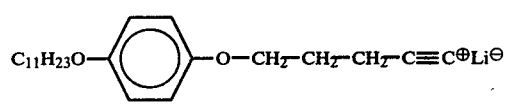

Into a 500 ml flask, fitted with a mechanical stirrer, a thermometer, and a dripper funnel, and maintained under a nitrogen atmosphere at −70° C., there were introduced:
150 ml of anhydrous THF,
11.7 ml of a 15% butyl-lithium solution in hexane (0.02745 mols of butyl-lithium).

The mixture was thereupon stirred at −70° C. and additioned dropwise with 10 g (0.02745 mols) of the product obtained as described under point A, in anhydrous THF.

At the end of the dripping, the temperature was allowed to spontaneously rise up and the mixture was left to rest overnight. The solution was used for the successive reaction without separating the lithium salt that had formed.

(C) Condensation between the lithium salt of 1-undecyloxy-4-[(pentynyl)-oxy]-benzene

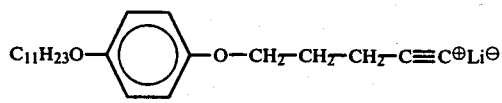

PO and methyl-chloromethylether CH₃—O—CH₂Cl.

To the solution containing the lithium salt obtained as described under point B, and maintained under constant stirring at −50° C., there were added dropwise 2.215 g (0.02745 mols) of methyl-chloromethyl ether.

The mixture was then allowed to spontaneously heat up to room temperature, whereupon it was poured into water and ice and extracted with ethyl ether.

The organic phase was then washed with water until reaching a neutral pH, was concentrated and then chromatographed on silica gel (eluent:hexane/ethyl ether in a 98:2 ratio). Thereby were obtained 4 g of the desired product (the NMR analysis proved consistent with the assigned structure).

EXAMPLE 2

Preparation of 1-decyloxy-4-[(7-oxa-4-octynyl)-oxy]-benzene (compound No. 1 Table 1).

(A) Preparation of 1-decyloxy-4-[(5-chloro-4-pentynyl)-oxy]-benzene

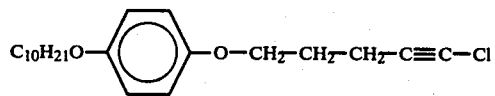

The compound was prepared starting from 4-decyloxy-phenol and 1,1,1,5-tetrachloropentane, operating as described in example 1, point A.

(B) Metalation of 1-decyloxy-4-[(5-chloro-4-pentynyl)-oxy]-benzene with butyl-lithium

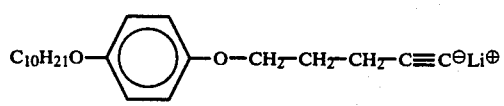

Into a 500 ml flask, fitted with a stirrer, a thermometer, a dripper funnel, were introduced, under a nitrogen atmosphere, 300 ml of anhydrous THF.

The THF was thereupon cooled down to −60° C. and to it were added dropwise 50 ml of a 15% solution of butyl-lithium in hexane, and, still by dripping, a solution of 24.2 g of decyloxy-4-[(5-chloro-4-pentynyl)-oxy]-benzene (obtained as described in point (A)) in 50 ml of anhydrous THF.

The reaction mixture was then stirred for 30 minutes at −60° C. and then at −20° C. until complete disappearance of the product of point (A) (gas-chromatographic control). The solution was then used for the successive reaction without separating the lithium salt.

(C) Condensation between the lithium salt of point (B) and methyl-chloromethyl-ether.

The solution containing the lithium salt obtained as described under point (B), was cooled down, still in a nitrogen atmosphere at −60° C., and to it were then added dropwise 5.9 g of methyl-chloromethyl-ether.

After 30 minutes of stirring at −60° C., the temperature was allowed to rise again to +20° C.

The solution was then diluted with water and neutralized with a 15% solution of hydrochloric acid. The organic phase was thereupon diluted with ethyl ether, separated, washed with water, anhydrified with anhydrous Na₂SO₄, concentrated and finally chromatographied on a silica gel column (eluent:petroleum ether/ethyl ether in a 95:5 ratio).

Thereby were obtained 15 g of the desired product (m.p. 33°–34° C.; NMR analysis consistent with the assigned structure).

EXAMPLE 3

Preparation of 6-(4-decyloxy-phenoxy)-2-hexynyl alcohol [compound No. 6, Table 1].

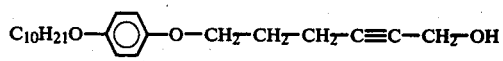

(A) Preparation of 5-(4-decyloxy-phenoxy)-1-pentyne

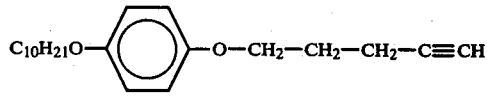

A solution of 5 g of 4-decyloxy-phenol in 10 ml of dimethyl-formamide (DMF) was added dropwise to a suspension of 1.28 g of ground KOH in 50 ml of DMF, maintaining the temperature at about 10° C. The reaction mixture was kept under constant stirring for 1 hour at the same temperature and was then cooled down to 0° C.

To the reaction mixture were then added 4.4 g of tosylate (p.toluensulphonate) of 4-pentynyl alcohol (CH≡C—CH₂—CH₂—CH₂—OH) in 10 ml of DMF. On completion of the addition, the temperature was allowed to spontaneously rise to room temperature and the reaction mixture was kept under stirring overnight, after which it was poured into water and ice and, finally, was extracted with ethyl ether. The etheric phase was separated, washed with a 5% NaOH solution and then with water until attaining a neutral pH. After anhydrifying, the solvent was eliminated under reduced pressure. Thereby were obtained 5.5 g of the desired product.

¹H NMR (CDCl₃, TMS):

δ(ppm): 0.9 (t, 3H, CH₃); 1.1–2.5 (m, 23H); 3.7–4.1 (m, 4H, CH₂—O—C₆H₄—O—CH₂); 6.7 (s, 4H, aromatic protons)

(s=singlet; t=triplet; m=multiplet or an uresolved complex signal).

(B) 9 g of the alkyne obtained as described under point (A) were dissolved in 40 ml of anhydrous tetrahydrofurane (THF). The solution was then cooled down to −5°–0° C. and was then additioned with 17.5 ml of 1.6 M solution of butyl-lithium in hexane, under stirring and in a nitrogen atmosphere. After a few minutes, the solution was additioned with 0.9 g of finely ground anhydrous formaldehyde. The reaction mixture was thereupon heated up to 60° C. for 3 hours, then poured into water and ice and extracted with ethyl ether.

After anhydrification the solvent was removed by distillation under reduced pressure. The raw product thus obtained was chromatographed on a silica gel column (eluent: petroleum ether/ethyl ether in the ratio 2:1).

There were thus obtained 7 g of 6-(4-decyloxy-phenoxy)-2-hexynyl alcohol.

IR (cm$^{-1}$): 3350 (OH), 2240 (—C≡C—);

$^1$H NMR (CDCl$_3$, TMS):

δ(ppm): 0.9 (t, 3H, CH$_3$); 1.1-2.6 (m, 20 H); 3.7-4.3 (m, 7H); 6.8 (s, 4H, aromatic protons)

(s=singlet, t=triplet, m=multiplet or an unresolved complex signal).

EXAMPLE 4

Preparation of 6-(4-decyloxy-phenoxy)-2-hexynyl cyclopropancarboxylate [compound No. 7, Table 1].

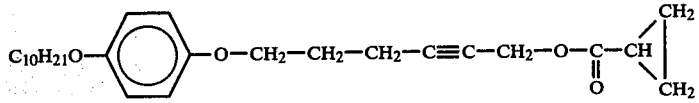

1 g of 6-(4-decyloxy-phenoxy)-2-hexynyl alcohol (obtained as described in example 3) was dissolved in 10 ml of anhydrous benzene containing 0.4 ml of pyridine.

To this solution were then added 0.3 g of cyclopropancarboxylic acid chloride. The reaction mixture was then subjected to stirring for 4 hours at room temperature, after which it was poured into water and ice.

The organic phase was separated, washed with water, with hydrochloric acid and with a saturated bicarbonate solution; finally it was anhydrified on anhydrous Na$_2$SO$_4$.

The solvent was then removed by distillation at reduced pressure and the residue was chromatographed on silica gel, thereby obtaining 1 g of the desired product.

$^1$H NMR (CDCl$_3$, TMS):

δ(ppm): 0.7-2.6 (m, 28H); 3.7-4.4 (m, 4H); 4.6 (t, 2H, ≡C—CH$_2$—O); 6.7 (s, 4H, aromatic protons)

(s=singlet; t=triplet, m=multiplet or unresolved complex signal).

EXAMPLE 5

Starting from the alcohol of example 3 and acetyl chloride or isobutyryl chloride and by operating as described in example 4, the following compounds have been prepared:

6-(4-decyloxy-phenoxy)-2-hexynyl acetate [compound No. 8, Table 1]

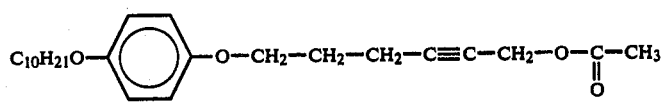

$^1$H NMR (CDCl$_3$, TMS):

δ(ppm): 0.9 (t, 3H, CH$_3$); 1.1-2.6 (m, 20 H); 2.0 (s, 3H, CH$_3$—COO); 3.7-4.0 (m, 4H, CH$_2$—O—C$_6$H$_4$—O—CH$_2$); 4.55 (t, 2H, ≡C—CH$_2$—O—CO); 6.7 (s, 4H, aromatic protons)

(s=singlet; d=doublet; t=triplet; m=multiplet or unresolved complex signal).

6-(4-decyloxy-phenoxy)-2-hexynyl isobutyrate [Compound No. 9, Table 1]

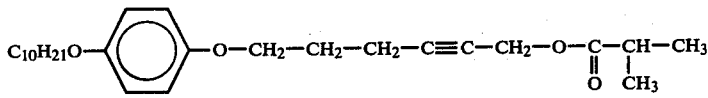

$^1$H NMR (CDCl$_3$, TMS):

δ(ppm): 0.9 (t, 3H, CH$_3$); 1.1 (d, 6H, CH$_3$—CH—CH$_3$); 1.1-2.7 (m, 21H); 3.7-4.0 (m, 4H, CH$_2$—O—C$_6$H$_4$—O—CH$_2$); 4.55 (t, 2H, ≡C—CH$_2$—O); 6.7 (s, 4H, aromatic protons)

(s=singlet, d=doublet, t=triplet, m=multiplet or unresolved complex signal).

EXAMPLE 6

Determination of the acaricide activity against mite eggs.

(A) Determination of the activity against *Tetranychus urticae* (eggs).

Foliar discs obtained from bean leaves were infested with mite eggs and subsequently treated by spraying with a hydroacetonic solution of the product under examination. The percentage of unhatched eggs was evaluated after 7 days from the treatment in comparison with the percentage of unhatched untreated eggs.

(B) Determination of activity against *Panonychus ulmi* (summer eggs).

Foliar discs, obtained from apple leaves, were infested with mite eggs, and subsequently treated by spraying with a hydroacetonic solution of the product under examination. The percentage of unhatched eggs was evaluated after 10 days from the treatment in comparison with the percentage of unhatched untreated eggs. The obtained results have been reported on Table 3.

EXAMPLE 7

Determination of the persistence of acaricide activity on *Panonychus ulmi* summer eggs.

Potted apple-trees, 3 years old, have been uniformly sprayed with aqueous-acetonic dispersions (containing a wetting agent) of the products under test (3 plants each product).

After drying, the plants have been transferred into a greenhouse wherein they have been kept for the period of the test.

At time intervals from the treatment, three leaves have been picked up from each plant and from every leaf a disc (25 mm diameter) has been cut off, corresponding to nine discs per treatment.

The foliar discs have been infested for eggs-laying with adult mites deriving from a field-collected resistant strain. After 24 hours, the adult mites have been removed and the foliar discs, infested with about a hundred eggs each, have been kept in a conditioned room at 24±1° C. and 65±5% relative humidity for about 10 days (till hatching).

For comparative purposes, a set of plants was treated with an aqueous-acetone solution and a wetting agent, without any active compound.

By operating in the same way as hereabove described a regular hatching of the mite eggs has been observed in the check series. The results of the test have been reported on Table 4.

EXAMPLE 8

Determination of the acaricide activity on winter eggs of *Panonychus ulmi*.

Twigs heavily infested with *P. ulmi* eggs have been cut off in autumn from apple-trees grown in an orchard naturally infested by mites.

The twigs have been then kept in the open under natural conditions.

During the winter, by operating in an unheated environment, from the twigs were cut small portion on which the presence of eggs was particularly concentrated and for each of these portions was counted the number of eggs that were clearly vital, removing all the damaged eggs and those of uncertain hatching.

With each of the compounds being tested were prepared suitable compositions and formulations, and with each of them were treated by spraying twenty twig-portions carrying about 800–1000 eggs in total.

After drying, the twig portions were kept in the open under a shelter in natural conditions until the end of the test. The results were assessed several days after the end of the hatching of the eggs in the check (portions of infested twigs treated only with a hydroacetonic solution and a surfactant), by counting the unhatched eggs in comparison with the eggs present before the treatment and taking into account the unhatched eggs in the check.

Following the same procedure, infested twig portions have been treated also with a commercial formulate containing Parathion in mineral oil.

Because of the fact that a certain number of mite eggs, both in the test and in the check, can be altered or missing for natural undefined causes, the results have been expressed by classes of activity rather than by percentage values that would not be suited for the practical character of the experiment. The obtained results have been reported on Table 5.

What we claim is:

1. A compound of general formula:

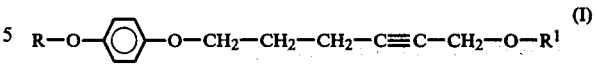 (I)

wherein
R represents an alkyl with from 8 to 11 carbon atoms;
R$^1$ represents a hydrogen atom, an alkyl with from 1 to 4 carbon atoms or an alkenyl with from 2 to 4 carbon atoms or

wherein
R$^2$ represents an alkyl with from 1 to 4 carbon atoms, a cycloalkyl with from 3 to 6 carbon atoms or phenyl.

2. A compound of formula:

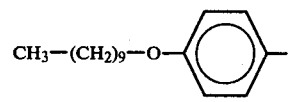

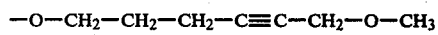

3. A compound of formula:

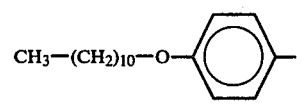

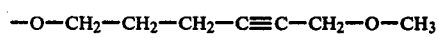

4. A compound of formula:

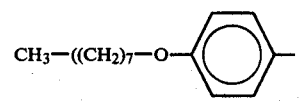

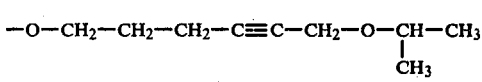

5. A compound of formula:

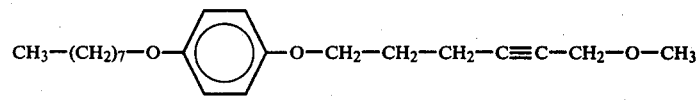

6. A compound of formula:

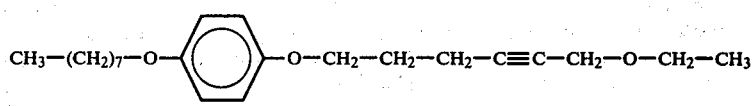

7. A compound of formula:

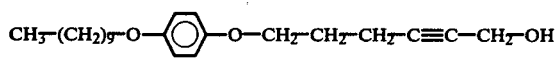

8. A compound of formula:

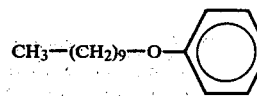

9. A compound of formula:

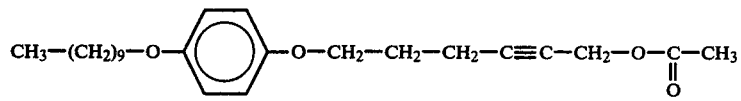

10. A compound of formula:

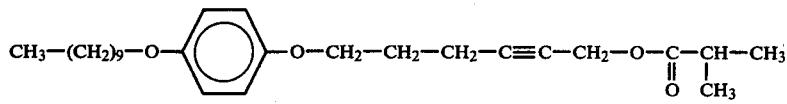

11. A compound of formula:

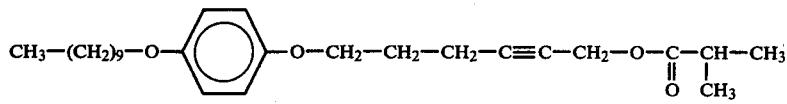

12. A method for controlling and preventing mite infestations on useful plants consisting in distributing on the plants an effective amount of a compound of general formula:

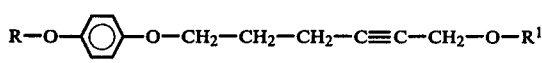

wherein
R represents an alkyl with from 8 to 11 carbon atoms;
$R^1$ represents a hydrogen atom, an alkyl with from 1 to 4 carbon atoms or an alkenyl with from 2 to 4 carbon atoms or

wherein
$R^2$ represents an alkyl with from 1 to 4 carbon atoms, a cycloalkyl with from 3 to 6 carbon atoms or phenyl as such or in the form of a suitable composition.

13. The method of claim 12 applied to the control of mites belonging to the Tetranychidae family.

14. A method for controlling and preventing mite infestations on useful plants consisting of treating the plants on which winter eggs of mites are present, with an effective amount of a compound of the following general formula I:

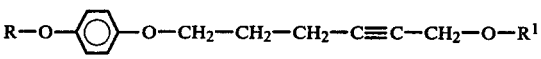

wherein

R is a $C_8$-$C_{11}$ alkyl;

$R^1$ is hydrogen, a $C_1$-$C_4$ alkyl, a $C_2$-$C_4$ alkenyl or

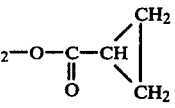

in which
$R^2$ is a $C_1$-$C_4$ alkyl, a $C_3$-$C_6$ cycloalkyl or phenyl.

15. The method of claim 14 applied to the control of mites belonging to the Tetranychidae family, genera Panonychus, Bryobia and Oligonychus.

16. The method of claim 14 applied to the control of mites belonging to the species *Panonychus ulmi*.

17. An acaricide composition containing, as active ingredient, a compound according to claim 1, and an inert carrier.

18. An acaricide composition containing, as active ingredient, a compound according to claim 1, an inert carrier, and at least one other additive selected from the group consisting of surfactants, wetting agents, adhesive agents and dispersants.

19. An acaricide composition according to claim 17, useful in the method of claim 15, and containing, in addition to the active ingredient of formula (I) and inert carrier, a liquid vehicle surfactant.

20. An acaricide composition according to claim 19, in which the liquid vehicle is an organic solvent selected from the group consisting of aromatic hydrocarbons, alkylaromatic hydrocarbons, alcohols and ketones.

21. An acaricide composition according to claim 19, consisting of 0.5 to 50 weight percent of a compound of formula (I), 30 to 80 weight percent of a liquid vehicle and 0.5 to 20 weight percent of a surfactant.

22. An acaricide composition according to claim 19, consisting of 0.5 to 30% weight percent of a compound of formula (I), 40 to 80 weight percent of a mineral oil, 5 to 30 weight percent of an organic solvent and 0.5 to 20 weight percent of a surfactant.

* * * * *